United States Patent [19]

Haneishi et al.

[11] Patent Number: 4,557,933
[45] Date of Patent: Dec. 10, 1985

[54] ANTIBIOTIC CALLED "CHLOROPOLYSPORIN", A PROCESS FOR ITS PREPARATION, AND ITS THERAPEUTIC AND VETERINARY USE

[75] Inventors: Tatsuo Haneishi; Takao Okazaki; Akio Torikata; Mutsuo Nakajima; Ryuzou Enokita; Toshiaki Katayama; Seigo Iwado, all of Hiromachi, Japan

[73] Assignee: Sankyo Company Limited, Tokyo, Japan

[21] Appl. No.: 627,439

[22] Filed: Jul. 3, 1984

[30] Foreign Application Priority Data

Jul. 15, 1983 [JP] Japan .................................. 58-128851

[51] Int. Cl.⁴ ......................... A61K 35/74; C12P 1/06
[52] U.S. Cl. ...................................... 424/118; 435/169
[58] Field of Search ......................... 424/118; 435/169

Primary Examiner—Jerome D. Goldberg
Attorney, Agent, or Firm—Frishauf, Holtz, Goodman & Woodward

[57] ABSTRACT

A novel compound, called chloropolysporin, has antibiotic properties and would appear to be a member of the class of glycopeptide antibiotics containing chlorine. It may be produced by cultivating a suitable strain of microorganism of the genus Micropolyspora, especially Micropolyspora sp. SANK 60983 (FERM BP-538). It may be combined with conventional pharmaceutically acceptable carriers or diluents for therapeutic use or incorporated into edible excipients, such as feed or water, for use as a growth-promoting agent, especially for farm animals.

7 Claims, 3 Drawing Figures

ANTIBIOTIC CALLED "CHLOROPOLYSPORIN", A PROCESS FOR ITS PREPARATION, AND ITS THERAPEUTIC AND VETERINARY USE

BACKGROUND OF THE INVENTION

The present invention relates to a new antibiotic, which we have called "chloropolysporin", to a process for its preparation by the cultivation of a newly discovered microorganism and to its use, both therapeutic, in the treatment and prophylaxis of infections caused by bacteria, and as a growth-promoting agent for animals.

As resistance to conventional antibiotics becomes increasingly established in common strains of pathogenic bacteria, the need for a wider variety of antibiotics for use in the fight against such bacteria becomes ever more crucial. Moreover, various antibiotics, for example chloramphenicol, aureomycin, vancomycin and avoparcin, have been administered or have been proposed for administration to poultry and other farm animals, including the ruminants and pigs, for the prophylaxis of disease or to promote growth of milk production. However, an inherent disadvantage of the use of antibiotics in this way is that there is some risk that traces of the antibiotics or of metabolic products thereof may be found in animal products intended for human consumption (such as eggs, milk or meat); the alleged dangers of such residues are increasingly criticized by some sections of the community. There is, accordingly, a considerable desire amongst farmers for an antibiotic substance which will have the desired growth-promoting effect but which will leave no or no significant residues in animal products.

We have now discovered a new microorganism, which we have assigned to the genus Micropolyspora, and which produces a new antibiotic substance that is highly effective against gram-positive bacteria and that shows considerable promise for use as a growth-promoting agent in animals.

BRIEF SUMMARY OF INVENTION

The new antibiotic substance of the invention is called "chloropolysporin" and, since its structure has not been elucidated, may be characterized by the following properties:
 (a) it takes the form of an amphoteric white powder, soluble in water;
 (b) specific rotation: $[\alpha]^{25} -94.4°$ (C=0.09, 50%V/V aqueous methanol, sodium D-line);
 (c) elemental analysis:
  C, 49.88%; H, 5.44%; N, 5.65%; Cl, 5.20%;
 (d) on acid hydrolysis it yields:
  neutral saccharides, glucose, mannose and rhamnose; amino acids; monochloro-monohydroxy-phenylglycine;
 (e) ultraviolet absorption spectrum:
  as illustrated in FIG. 1 of the accompanying drawings, having absorption maxima $\lambda_{max}$ at 280 nm ($E_{1cm}=45$) in a 0.01N solution of hydrochloric acid and at 300 nm ($E_{1cm}=54.2$) in a 0.01N aqueous solution of sodium hydroxide, the absorbences, E, being measured at a concentration of 1% w/v;
 (f) infrared absorption spectrum:
  the infrared absorption spectrum ($\nu cm^{-1}$) measured on a KBr disc is as shown in FIG. 2 of the accompanying drawings;
 (g) nuclear magnetic resonance spectrum:
  the nuclear magnetic resonance spectrum ($\delta ppm$) measured at 400 MHz in a mixture of deuterium oxide and deuterohydrochloric acid of pH value about 3.0, using sodium 2,2-dimethyl-2-silapentane-5-sulfonate as the internal standard, is as illustrated in FIG. 3 of the accompanying drawings;
 (h) solubility:
  soluble in water and methanol, sparingly soluble in acetone, and insoluble in ethyl acetate, chloroform and benzene;
 (i) color reactions:
  positive in Ninhydrin and Rydon-Smith reactions;
 (j) thin layer chromatography;
  Rf value=0.65, using a cellulose sheet (Eastman) as adsorbent and a 15:10:3:12 by volume mixture of butanol, pyridine, acetic acid and water as the developing solvent;
 (k) high voltage paper electrophoresis:
  using Toyo's filter paper No. 51A in a 0.1M tris-hydrochloric acid buffer solution of pH 7.5 (3300 volt/60 cm, 1 hour); the migration distance (detected by bioautography with Bacillus subtilis PCI 219) from the origin to the cathode was 4 cm.

The invention also provides a process for producing chloropolysporin by cultivating a chloropolysporin-producing microorganism of the genus Micropolyspora in a culture medium therefor and collecting chloropolysporin from the culture broth.

The invention still further provides a pharmaceutical or veterinary composition comprising chloropolysporin in admixture with a pharmaceutical or veterinary carrier or diluent.

The invention still further provides a method for the treatment or prophylaxis of bacterial infections by administering chloropolysporin to an animal, which may be human or non-human.

The invention still further provides a method of promoting the growth of a farm animal by the oral administration of chloropolysporin thereto.

DETAILED DESCRIPTION OF INVENTION

Figure 1:
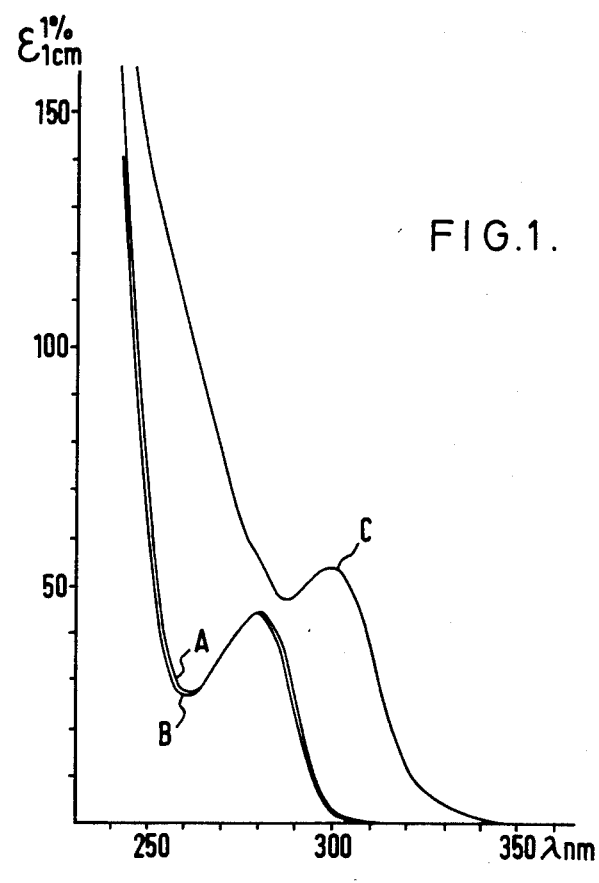

Chloropolysporin is produced by the cultivation of a newly discovered Micropolyspora strain herein identified as Micropolyspora sp. strain SANK 60983, which was isolated from a soil sample collected in Tochigi Prefecture, Japan.

The newly discovered microorganism, Micropolyspora sp. strain SANK 60983, has the characteristics described hereafter. These characteristics were determined by cultivation on various media prescribed by the ISP (International Streptomyces Project) or with the media recommended by S. A. Waksman in Volume 2 of "The Actinomycetes", in all cases at a temperature of 28° C.

1. Morphological Characteristics

Strain SANK 60983 grows relatively well on various media. The aerial mycelium is hardly visible on almost all media but may occasionally be visible on glycerol-asparagine agar or on potato extract-carrot extract agar. The aerial and vegetative mycelia bear, at the top and the middle, short chains of spores, normally from 1 to 20, although occasionally more than 20, spores. No distinct fragmentation of the hyphae is observed with the strain, although it may be observed during later stages of the culture.

2. Culture Characteristics

Strain SANK 60983 can produce pale yellow, yellowish-brown or yellowish-gray colours. Aerial hyphae are not observed on most media, although white aerial hyphae are produced on some media. No soluble pigment is produced. Table 1 shows the results obtained after cultivation for 14 days at 28° C. on various standard culture media. The color names and numbers used were assigned according to the "Guide to Color Standard", a manual published by Nippon Shikisai Kenkyusho, Tokyo, Japan.

TABLE 1

| Medium | Growth | Aerial Mycelium | Reverse | Soluble Pigment |
|---|---|---|---|---|
| Yeast extract-malt extract agar (ISP 2) | Abundant, raised, wrinkled, yellowish-brown (8-8-8) | None | Yellowish-brown (8-8-8) | None |
| Oatmeal agar (ISP 3) | Good, smooth, dull yellow (8-8-9) | None | Dull yellow (8-8-9) | None |
| Inorganic salt-starch agar (ISP 4) | Abundant, smooth, yellowish-gray (2-9-10) to pale yellowish-brown (6-8-9) | None | Yellowish-gray (2-9-10) to pale yellowish-brown (6-8-9) | None |
| Glycerol-asparagine agar (ISP 5) | Good, wrinkled, yellowish-brown (2-9-10) | Poor, white | Yellowish-brown (2-9-10) | None |
| Peptone-yeast extract-iron agar (ISP 6) | Moderate, smooth, pale brown (2-8-9) | None | Pale yellowish-brown (4-8-9) | None |
| Tyrosine agar (ISP 7) | Abundant, raised, wrinkled, pale yellowish-brown (14-8-9) | None | Dull yellow (10-8-8) | None |
| Sucrose nitrate agar | Abundant, raised, wrinkled, pale yellow (12-8-10) | None | Pale yellowish-brown (4-8-8) | None |
| Glucose-asparagine agar | Moderate, smooth, yellowish-gray (2-9-10) | None | Yellowish-gray (2-9-10) | None |
| Nutrient agar (Difco) | Moderate, smooth, pale yellowish-brown (6-8-9) | None | Pale yellowish-brown (6-8-9) | None |
| Water agar | Poor, smooth, yellowish-gray (1-9-10) | None | Yellowish-gray (1-9-10) | None |
| Potato extract-carrot extract agar | Moderate, smooth, yellowish-gray (2-9-10) | Poor, white | Yellowish-gray (2-9-10) | None |

3. Physiological Properties

The physiological properties of strain SANK 60983 are shown in Table 2.

TABLE 2

| | | |
|---|---|---|
| Decomposition: | Adenine | − |
| | Casein | + |
| | Xanthine | − |
| | Hypoxanthine | + |
| | Urea | + |
| Hydrolysis of starch | | ± |
| Liquefaction of gelatin | | + |
| Coagulation of milk | | − |
| Peptonization of milk | | − |
| Reduction of nitrates | | + |
| Secretion of deoxyribonuclease | | + |
| Melanin formation: | ISP 1 | − |
| | ISP 6 | − |
| | ISP 7 | − |
| Acid production from: | Sodium Acetate | − |
| | Sodium Succinate | − |
| | Sodium Citrate | − |
| | Sodium Pyruvate | − |
| | Sodium Tartarate | − |
| | D-Glucose | + |
| | L-Arabinose | + |
| | D-Xylose | + |
| | Inositol | + |
| | D-Mannitol | + |
| | D-Fructose | + |
| | L-Rhamnose | + |
| | Sucrose | + |
| | Raffinose | ± |
| Utilization of carbon sources: | D-Glucose | + |
| | L-Arabinose | + |
| | D-Xylose | + |
| | Inositol | + |
| | D-Mannitol | + |
| | D-Fructose | + |
| | L-Rhamnose | + |
| | Sucrose | + |
| | Raffinose | ± |
| Growth in NaCl: | 3% w/v | + |
| | 5% w/v | ± |
| | 7% w/v | ± |
| | 10% w/v | − |
| Range of growth temperature: | 10° C. | − |
| | 20° C. | + |
| | 28° C. | + |
| | 37° C. | + |
| | 45° C. | − |

In the above Table, "+" means positive, "−" means negative and "±" means slightly positive.

Although coagulation and peptonization of milk are both reported as negative, they may occasionally turn positive after long-term culture.

4. Whole Cell Components

Acid hydrolyzates of bacterial cells were assayed by paper chromatography, using the method of M. P. Lechevalier et al. ["The Actinomycetes Taxonomy", page 225 (1980)]. meso-Diaminopimelic acid, arabinose and galactose were found to be present in the cell walls, which are thus of Type IV, whilst the whole cell sugar pattern is of Type A. The characteristic acyl group of the cell wall was also investigated by the method of Uchida et al. [(J. Gen. Appl. Microbiol, 23,249 (1977)] and found to be the acetyl group.

None of the known genera of actinomycetes has been reported to be capable of forming spores in the middle of the hyphae. However, from a comparison of other characteristics, the new strain is clearly related to the genera Actinopolyspora, Saccharopolyspora, Pseudocardia and Micropolyspora. However, both Actinopolyspora and Saccharopolyspora allow spores to grow only on the tips of aerial hyphae, and the former is a highly halophilic genus, whilst the characteristic acyl group of the cell wall of the latter is the glycolyl group. For these reasons, the new strain SANK 60983 cannot be assigned to either of these genera. Although strains of the genus Pseudonocardia can grow spores on the aerial hyphae and on the vegetative mycelium, as does strain SANK 60983, the site of its growth takes place only at the tip of the hyphae and, moreover, its hyphae characteristically grow by budding; thus, strain SANK 60983 cannot be assigned to the genus Pseudonocardia.

The only difference between the genus Micropolyspora and strain SANK 60983 is that the site of growth of spores of Micropolyspora is limited to the tips of the hyphae, whereas that of SANK 60983 is at both the tip and the middle of the hyphae.

At the present time, when there has been virtually no discussion in learned circles as to the implications for taxonomy of difference of this type, it would seem inappropriate to differentiate between genera solely on the basis of differences in the site of growth of their spores. Accordingly, it seems most satisfactory to regard the strain SANK 60983 as representative of a new species of the genus Micropolyspora and it has, accordingly, been named Micropolyspora sp. SANK 60983. It should, however, be remembered that assignment of a strain of microorganism to any particular species, genus or even family is largely a matter of consensus amongst those experienced in the study of the particular class of microorganism involved and the original assignment of a microorganism can be, and not infrequently is, changed after wider discussion.

The strain SANK 60983 has been deposited with the Fermentation Research Institute, Agency of Industrial Science and Technology, Ministry of International Trade and Industry, Japan, on 10th March 1983 under the accession No. FERM P-6985 and was re-deposited in accordance with the conditions stipulated by the Budapest Treaty with said Fermentation Research Institute on 4th June 1984 under the accession No. FERM BP-538.

It has been established that strain SANK 60983 produces chloropolysporin. However, as is well known, the properties of microorganisms falling within the general category of the Actinomycetes can vary considerably and such microorganisms can readily undergo mutation, both through natural causes and as the result of induction by artificial means. Accordingly, the process of the present invention embraces the use of any microorganism which can be classified within the genus Micropolyspora and which shares with the new strain SANK 60983 the characteristic ability to produce chloropolysporin.

The cultivation of microorganisms of the genus Micropolyspora in accordance with the present invention to produce chloropolysporin can be performed under conditions conventionally employed for the cultivation of Actinomycetes species, preferably in a liquid culture, and desirably with shaking or stirring and aeration. The nutrient medium used for the cultivation is completely conventional and contains such constituents as are commonly used in the cultivation of the Actinomycetes. Specifically, the medium should contain an assimilable carbon source, suitable examples of which include glucose, maltose, sucrose, mannitol, molasses, glycerol, dextrin, starch, soybean oil and cottonseed oil; an assimilable nitrogen source, suitable examples of which include soybean meal, peanut meal, cottonseed meal, fish meal, corn steep liquor, peptone, meat extract, pressed yeast, yeast extract, sodium nitrate, ammonium nitrate or ammonium sulfate; and one or more inorganic salts, such as sodium chloride, phosphates, calcium carbonate and trace metal salts. Where cultivation is effected in a liquid medium, it is generally desirable to incorporate an anti-foaming agent (for example silicone oil, vegetable oil or a suitable surfactant) in the medium.

The cultivation is suitably performed at a substantially neutral pH value and at a temperature of from 24° to 30° C., more preferably at about 28° C.

The production of chloropolysporin as cultivation proceeds may be monitored by a variety of conventional techniques for monitoring the production of antibiotics by microbial culture and which require little or no elaboration here. A suitable technique might be the paper disc test method (using, for example, a paper disc of diameter about 8 mm produced by Toyo Kagaku Sangyo Co., Ltd) and using *Bacillus subtilis* PCI 219 or *Staphylococcus aureus* FDA 209P JC-1 as the test organism.

The amount of chloropolysporin produced normally reaches a maximum after cultivation has proceeded for 55-70 hours and it is clearly desirable to separate the chloropolysporin from the culture medium no later than the time when this maximum has been reached. However, this period may vary, depending upon the cultivation conditions and techniques, and a shorter or longer period may be appropriate, depending upon the circumstances. The correct cultivation time may readily be assessed for every case by routine experiment, using suitable monitoring techniques, e.g. as described above.

Chloropolysporin is mainly released into the liquid portion of the culture broth and can thus be recovered by removing solid matter, including the mycelium, for example by filtration, preferably using a filter aid such as diatomaceous earth, or by centrifugation. It can then be recovered from the separated liquid portion by conventional techniques and, if desired, then purified.

Chloropolysporin is preferably separated from other products in said liquid portion by means of an adsorbent, either by adsorbing the impurities or by adsorbing the chloropolysporin or by adsorbing both separately or together and then eluting the chloropolysporin. A wide range of adsorbents may be used; examples which we have found to be particularly satisfactory include: activated carbon; Amberlite (registered trade mark) XAD-2, XAD-4 or XAD-7 (products of Rohm and Haas); and Diaion (registered trade mark) HP 10, HP 20, HP 20AG or HP 50 (products of Mitsubishi Chemical Industries Co., Ltd.). The impurities present in the liquid portion may be removed by passing the solution containing chloropolysporin through a layer or column of one or more of the aforementioned adsorbents or by adsorbing chloropolysporin on one or more of the adsorbents and then eluting the chloropolysporin with a suitable eluent. Suitable eluents include mixtures of methanol, acetone or butanol with water.

The chloropolysporin obtained may be further purified by various means. Suitable methods include: partition column chromatography using a cellulose product, such as Avicel (a registered trade mark for a product of Asahi Chemical Industry Co., Ltd.) or Sephadex LH-20 (a registered trade mark for a product of Farmacia, Sweden); reverse phase column chromatography using a carrier for the reverse phase; extraction based on the difference in distribution in solvents between chloropolysporin and its contaminating impurities; or the counter-current distribution method. These purification techniques may be used singly or in combination and may, if needed, be repeated one or more times.

Depending upon the culture conditions, chloropolysporin can exist in the mycelium from the culture broth and can be extracted therefrom by conventional techniques. For example, it can be extracted with a hydrophilic organic solvent (such as an alcohol or acetone), and then the solvent removed from the extract to leave a residue, which is dissolved in an aqueous medium. The chloropolysporin can be extracted from the resulting solution and purified as described above.

Chloropolysporin thus obtained has the physical and chemical properties described above. Its minimal inhibitory concentration (MIC) against various gram-positive and gram-negative bacteria was determined by the agar dilution method, using a Mueller-Hinton agar medium containing 2% w/w glycerol (produced by Difco); the MIC against anaerobic bacteria was determined using a GAM agar medium (produced by Nissui). The results are shown in Tables 3 and 4.

TABLE 3

| Test strain | | MIC (μg/ml) |
|---|---|---|
| Staphylococcus aureus | FDA 209P JC-1 | 1.56 |
| Staphylococcus aureus | SANK 70175 | 3.13 |
| Staphylococcus aureus Smith | | 3.13 |
| Staphylococcus epidermidis | SANK 71575 | 6.25 |
| Streptococcus faecalis | SANK 71778 | 1.56 |
| Bacillus subtilis | PCI 219 | 0.39 |
| Mycobacterium smegmatis | ATCC 607 | 12.5 |
| Escherichia coli | NIHJ JC-2 | >100 |
| Klebsiella pneumoniae | PCI 602 | >100 |
| Pseudomonas aeruginosa | NCTC 10490 | >100 |
| Serratia marcescens | SANK 73060 | >100 |
| Proteus mirabilis | SANK 70461 | >100 |

TABLE 4

| Test strain | MIC (μg/ml) |
|---|---|
| Bacteroides fragilis | >100 |
| Eubacterium aerofaciens | 0.39 |
| Fusobacterium necrophorum | >100 |
| Peptostreptococcus micros | 0.78 |
| Peptostreptococcus parvulus | 0.39 |
| Propionibacterium acnes | 0.78 |
| Clostridium botulinum | 0.78 |
| Clostridium sordellii | 0.20 |
| Clostridium histolyticum | 0.78 |
| Clostridium difficile | 0.78 |

From the results given in the above Tables, it can be seen that chloropolysporin is effective against gram-positive bacteria, such as *Staphylococcus aureus, Staphylococcus epidermidis, Streptococcus faecalis, Bacillus subtilis* and *Mycobacterium smegmatis*, and against anaerobic gram-positive bacteria, such as *Eubacterium aerofasciens, Peptostreptococcus micros, Propionibacterium acnes, Clostridium botulinum, Clostridium sordellii* and *Clostridium difficile*.

Prophylactic Activity In Mice

*Staphylococcus aureus* Smith was cultured overnight in tryptosoy bouillon medium (tryptosoy is a trypsin-solubilized soy, sold by Eiken Co. Ltd., Japan). This was then inoculated intraperitoneally, together with mucin at a concentration of 5% w/v, in an amount of $2.8 \times 10^6$ cells per test mouse. The mice employed were male 5 week old mice of the ICR/JCL strain and were employed in groups of 10 for each test. Both immediately after and 4 hours after the inoculation, an aqueous solution of chloropolysporin at various concentrations was injected subcutaneously. The prophylactic efficiency of chloropolysporin was clearly apparent and its $ED_{50}$ value was 11.7 mg/kg.

Acute Toxicity

The $LD_{50}$ value of chloropolysporin on intravenous injection into male 5 week old mice of the ICR/JCL strain (employed in groups 10 for each test) was 375 mg/kg and no adverse effect was observed on subcutaneous injection up to a dose of 1000 mg/kg.

Comparison of the properties, chemical, physical and biological, given above of chloropolysporin with those of known antibiotics suggests that it may be similar to the glycopeptide antibiotics containing chlorine, such as Vancomycin, Avoparcin α and β, Actinoidin A and B or A-35512 B. However, chloropolysporin can be clearly distinguished from these known antibiotics on the basis of the differences shown in the following Table 5. Specifically, it has different neutral saccharide components and different amino acids are produced on acid hydrolysis. Moreover, it moves a different distance on high voltage paper electrophoresis (3300 volts/60 cm, 1 hour, pH 7.5, in 0.1M tris-hydrochloric acid buffer solution), and it has a different chlorine content.

TABLE 5

| Antibiotics | Neutral saccharides | Amino acids | Distance | Chlorine content |
|---|---|---|---|---|
| Vancomycin | Glucose | Aspartic acid N—methyl-leucine | | 4.89 |
| Avoparcin α | Glucose, Mannose, Rhamnose | 3-Hydroxy-phenylglycine | 9.4 cm | 1.85 |
| Avoparcin β | Glucose, Mannose, Rhamnose | 2-Chloro-3-hydroxyphenyl-glycine | 9.4 cm | 3.65 |
| Actinoidin A | Glucose, Mannose | 3-Hydroxy-phenylglycine, Phenylalanine | | 2.02 |
| Actinoidin B | Glucose, Mannose, | 2-Chloro-3-hydroxyphenyl-glycine, Phenylalanine | | 3.96 |
| A-35512B | Glucose, Mannose, Rhamnose, Fucose | | | 1.82 |
| Actaplanin | Glucose, Mannose Rhamnose | | | 1.96 |
| Ristocetin A | Glucose, Mannose Rhamnose Arabinose | | | 0 |
| Ristocetin B | Glucose, Mannose, Rhamnose | | | 0 |
| Chloropolysporin | Glucose, Mannose, | Monochloro-monohydroxy- | 4 cm | 5.20 |

TABLE 5-continued

| Antibiotics | Neutral saccharides | Amino acids | Distance | Chlorine content |
|---|---|---|---|---|
| | Rhamnose | phenylglycine | | |

The value reported above as "Distance" is the distance of movement on high voltage paper electrophoresis, measured using bioautography with *Bacillus substilis* PCI 219 as the test organism.

From the above findings, it can be seen that chloropolysporin can be used as an antibiotic against various diseases caused by bacterial infections. The route of administration can vary widely and may be parenteral (e.g. by subcutaneous, intravenous or intramuscular injection or by suppository) or oral (in which case it may be in the form of a tablet, capsule, powder or granule). The dose will, of course, vary with the nature of the disease to be treated, the age, condition and body weight of the patient and the route and time of administration; however, for an adult human patient, a daily dose of from 0.1 to 10 grams is preferred and this may be administered in a single dose or in divided doses.

Moreover, in view of the strong activity of chloropolysporin against infectious bacteria of the genus Costridium, it can be prepared to be a valuable growth-promoting agent for veterinary use. Bacteria of the genus Clostridium, particularly *Clostridium perfringens* and *Clostridium difficile* are often present in the intestines of farm animals and are the cause of diarrhoea. Since chloropolysporin has a strong activity against such microorganisms, it would suppress their growth in the intestines and thus improve the microbial balance of the intestines. This, in turn, would improve feed efficiency, thus contributing to weight gain and improved milk production in various farm animals, including ruminants, pigs and poultry. Moreover, chloropolysporin, in common with the other glycopeptide antibiotics, is likely to have a low rate of absorption through the digestive organs and, as a result, where chloropolysporin is administered in the feed, little will remain in the animal body and hence in animal products, such meat, milk or eggs. When chloropolysporin is used as a growth-promoting agent for animals, it is preferably administered orally. Although it may be formulated into an edible composition with any suitable carrier or diluent, it is particularly convenient to administer it in admixture with an animal feed or with drinking water. When the chloropolysporin is used as a feed additive, it may be mixed alone with the feed or it may be mixed in combination with other non-toxic edible excipients, nutrient supplements (e.g. vitamins, minerals or amino-acids), other antibiotics, anticoccidal agents or enzymes. For administration to animals as a growth-promoting agent, the chloropolysporin need not necessarily be in a completely purified form and it may be used in a crude or partially purified form, as obtained at any desired stage during the extraction and purification described above. For use as a growth-promoting agent, chloropolysporin is preferably employed in an amount of from 1 to 200, more preferably from 5 to 60, ppm by weight on the basis of the feed, drinking water or other carrier to which it is added; where an impure form of chloropolysporin is employed, a concentration having equivalent activity is used.

Animals to which chloropolysporin can be administered include farm mammals (e.g. cattle, horses, swine, sheep and goats), poultry (e.g. chickens, turkeys and ducks) and pet animals (e.g. dogs, cats and birds). Most significantly, when chloropolysporin is administered orally to animals, their growth is effectively promoted, but it is little absorbed from the gastro-intestinal tract and it exhibits low retention in animal tissues: thus, there is an almost complete absence of chloropolysporin residues in the products (e.g. milk, meat or eggs) of animals to which it has been administered, which is a great advantage from the view point of food hygiene.

The invention is further illustrated by the following examples.

EXAMPLE 1

PREPARATION OF CHLOROPOLYSPORIN

One loopful of Micropolyspora sp. SANK 60983 was inoculated into a 500 ml Erlenmeyer flask containing 80 ml of medium A, which has the following composition (percentages are by weight):

| MEDIUM A | |
|---|---|
| Glucose | 3% |
| Pressed yeast | 1% |
| Soybean meal | 3% |
| Calcium carbonate | 0.4% |
| Magnesium sulfate | 0.2% |
| Anti-foaming agent (Nissan CB-442) | 0.01% |
| Water | the balance |
| (adjusted to pH 7.0) | |

The microorganism was then cultured for 84 hours at 28° C., using a rotary shaker at 220 r.p.m.

4 ml of the resulting seed culture were inoculated into a 500 ml Erlenmeyer flask containing 80 ml of medium B, which has the following composition. (percentages are by weight):

| MEDIUM B | |
|---|---|
| Glucose | 5% |
| Yeast extract | 0.1% |
| Soybean meal | 1% |
| Polypepton (a Product of Daigo Eiyo Co. Ltd., Japan) | 0.4% |
| Beef extract | 0.4% |
| Sodium chloride | 0.25% |
| Calcium carbonate | 0.5% |
| Anti-foaming agent (Nissan CB-442) | 0.01% |
| Water | the balance |
| (adjusted to pH 7.2) | |

The microorganism was then cultured at 28° C. for 60 hours, using a rotary shaker at 220 r.p.m.

At the end of this time, batches of culture broth separately cultivated as described above were combined to give a total of 3 liters of culture broth. Celite 545 (a registered trade mark for a product of Johns-Manville Products Corp., New Jersey, U.S.A.) filter aid was added to the culture broth and the mixture was filtered, to give 2.8 liters of a filtrate having a pH value of 7.3. This filtrate was adsorbed on 280 ml of Diaion HP 20 (a product of Mitsubishi Chemical Industries Co., Ltd.), and the adsorbent was washed with water and then eluted with 50% v/v aqueous acetone, yielding 720 ml of fractions showing antibiotic activity. The combined active fractions were condensed by evaporation under reduced pressure to a volume of 115 ml; and the concentrate was adjusted to a pH value of 4.0 and then adsorbed on 280 ml of Dowex 50W×4(H+) (a registered trade mark for a product of Dow Chemical Co., Michigan, U.S.A.) and eluted with water. The solution thus obtained was lyophilized, giving 2.6 g of a crude powder.

1.3 g of this crude powder were dissolved in water and then adsorbed by passage through a column containing 360 ml of Diaion HP 20, which had previously been equilibrated with a 40:60 by volume mixture of methanol and a 0.5% w/v aqueous solution of sodium chloride. The product was then eluted from the column with the same mixture as was used for the equilibration, in fractions of about 14 ml each, up to fraction 80. Fractions 26-58 showed antibiotic activity and were collected to give a total volume of about 470 ml. Methanol was distilled off under reduced pressure from the combined active fractions and the residue was adsorbed in a column containing 35 ml of Diaion HP 20. This was washed with water and then eluted with 50% v/v aqueous acetone and the active fractions were collected. Acetone was distilled from the collected active fractions under reduced pressure and the residue was lyophilized, to give 230.9 mg of a powder.

This powder was adsorbed in a column containing 80 ml of SE-Sephadex C-25 (a registered trade mark for a product of Farmacia, Sweden), which had previously been equilibrated with a 0.02M ammonium formate buffer solution having a pH of 3.0. The column was then washed with 0.05M and 0.1M ammonium formate buffer solutions each having a pH of 3.0, after which it was eluted with a 0.2M ammonium formate buffer solution having a pH of 3.0, to give 520 ml of active fractions.

These active fractions were adsorbed in a column containing 35 ml of Diaion HP 20, which was washed with water and then eluted with 50% v/v aqueous acetone. Acetone was distilled from the resulting active fractions under reduced pressure, and the residue was lyophilized, to give 137 mg of chloropolysporin in the form of a white powder having the properties heretofor described.

EXAMPLE 2

PREPARATION OF CHLOROPOLYSPORIN

One loopful of Micropolyspora sp. SANK 60983 was inoculated into a 500 ml Erlenmeyer flask containing 80 ml of Medium A, and then cultured for 84 hours at 28° C., using a rotary shaker at 220 r.p.m. 25 ml of the resulting seed culture were inoculated into each of four 2 liter Erlenmeyer flasks, each containing 500 ml of Medium B, and cultured at 28° C. for 24 hours. 750 ml of the resulting culture broth were inoculated into each of two jar fermenters, each having a capacity of 30 liters and each containing 15 liters of Medium B. The microorganism was then cultivated for 69 hours with aeration (at the rate of 15 liters of air per minute) and stirring (at the rate of 150 r.p.m.).

Celite 545 filter aid was added to the resulting combined 30 liters of culture broth and filtered, to give 30 liters of filtrate. This filtrate was adsorbed onto 3 liters of Diaion HP 20, washed with water and then eluted with 50% v/v aqueous acetone. The active fractions were collected and combined and the acetone was distilled off under reduced pressure. The residue was lyophilized, to give 44 g of a crude powder.

41 g of this powder were dissolved in water and adsorbed into 1.8 liters of Diaion HP 20, washed with 5 liters of water and 20 liters of 10% v/v aqueous acetone, and then eluted with 4 liters of 50% v/v aqueous acetone. The active fractions from the elution were collected and condensed to a volume of 1 liter by evaporation under reduced pressure. The condensate was centrifuged at 5000 r.p.m. and the resulting precipitate was dried, to give 9.6 g of crude chloropolysporin powder.

This crude powder was dissolved in 1 liter of 50% v/v aqueous methanol and then adsorbed onto 200 ml of acidic alumina (a product of Burroughs Wellcome & Co.), which had previously been equilibrated with 50% v/v aqueous methanol. The adsorbed product was then eluted with the same solvent, and the active fractions, a total of 1.1 liters, were collected. The combined active fractions were passed through 60 ml of Dowex 21K (OH$^-$), and eluted with water. The active fractions, a total volume of 1.2 liters, were collected and then condensed by evaporation under reduced pressure to a volume of 30 ml. This condensate was lyophilized, to give 1.23 g of powder. The powder was dissolved in aqueous hydrochloric acid of pH 4.0 and then adsorbed onto 56 g of Polyamide filled with water (a product of Burroughs Wellcome & Co.). This was subjected to gradient elution with 400 ml of water and 1.2 liters of methanol, in 20 ml fractions, up to fraction 80. Fractions 30-60 were collected and combined. The methanol was distilled off under reduced pressure and the resulting concentrate was lyophilized, to give 738 mg of chloropolysporin in the form of a white powder having the properties heretofor described.

EXAMPLE 3

| CAPSULES FOR ORAL USE |  |
|---|---|
| The following ingredients were mixed: | |
| Chloropolysporin | 100 mg |
| Lactose | 100 mg |
| Corn starch | 148.5 mg |
| Magnesium stearate | 1.5 mg |

The mixture was sieved through a 30 Tyler standard mesh sieve, giving 350 mg of a fine powder, which was put into a No. 2 gelatin capsule.

Figure 2:
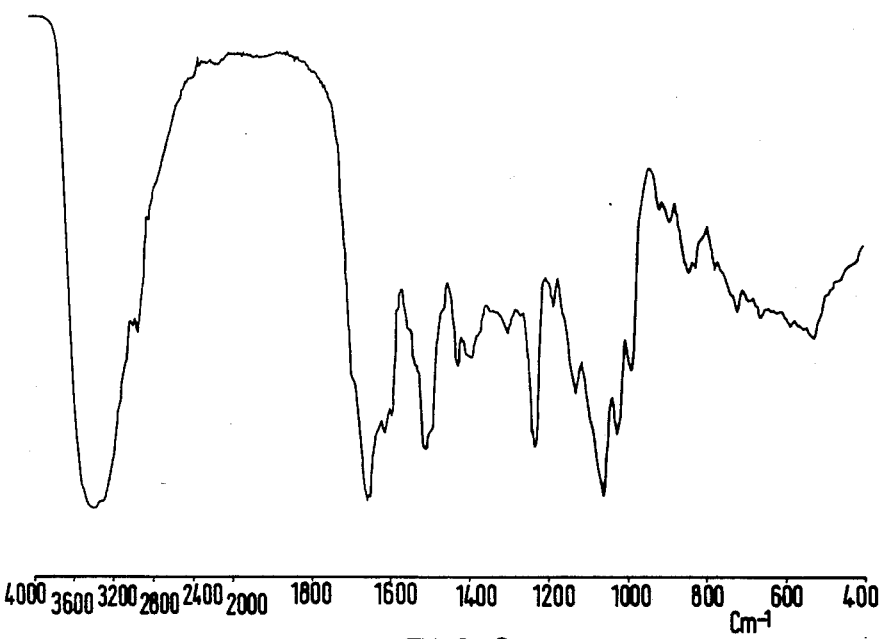
Figure 3:
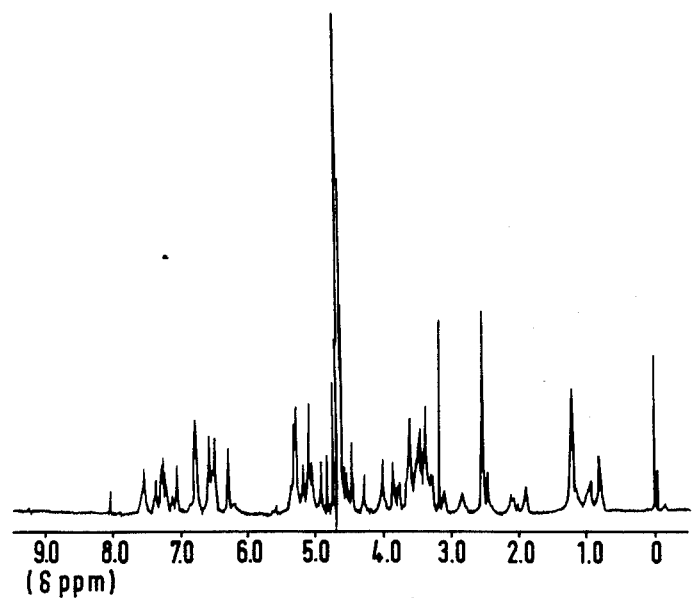

What is claimed is:

1. An antibiotic substance named chloropolysporin and characterized by the following properties:
   (a) it takes the form of an amphoteric white powder, soluble in water;
   (b) specific rotation: $[\alpha]^{25} -94.4°$ (C=0.09, 50%v/v aqueous methanol, sodium D-line);
   (c) elemental analysis:
   C, 49.88%; H, 5.44%; N, 5.65%; Cl, 5.20%;
   (d) on acid hydrolysis it yields:
   neutral saccharides: glucose, mannose and rhamnose; amino acids: monochloro-monohydroxyphenylglycine;
   (e) ultraviolet absorption spectrum:
   as illustrated in FIG. 1 of the accompanying drawings, having absorption maxima $\lambda_{max}$ at 280 nm ($E_{1cm}=45$) in a 0.01N solution of hydrochloric acid and at 300 nm ($E_{1cm}=54.2$) in a 0.01N aqueous solution of sodium hydroxide, the absorbences, E, being measured at a concentration of 1% w/v;
   (f) infrared absorption spectrum:
   the infrared absorption spectrum ($\nu cm^{-1}$) measured on a KBr disc is as shown in FIG. 2 of the accompanying drawings;

(g) nuclear magnetic resonance spectrum:

the nuclear magnetic resonance spectrum (δppm), measured at 400 MHz in a mixture of deuterium oxide and deuterohydrochloric acid of pH value about 3.0, using sodium 2,2-dimethyl-2-silapentane-5-sulfonate as the internal standard, is as illustrated in FIG. 3 of the accompanying drawings;

(h) solubility:

soluble in water and methanol, sparingly soluble in acetone, and insoluble in ethyl acetate, chloroform and benzene;

(i) color reactions:

positive in Ninhydrin and Rydon-Smith reactions;

(j) thin layer chromatography:

Rf value=0.65, using a cellulose sheet (Eastman) as adsorbent and a 15:10:3:12 by volume mixture of butanol, pyridine, acetic acid and water as the developing solvent;

(k) high voltage paper electrophoresis:

using Toyo's filter paper No. 51A in a 0.1M tris-hydrochloric acid buffer solution of pH 7.5 (3300 volt/60 cm, 1 hour); the migration distance (detected by bioautography with *Bacillus subtilis* PCI 219) from the origin to the cathode was 4 cm.

2. A process for producing the antibiotic substance chloropolysporin as defined in claim 1, which comprises cultivating under aerobic conditions Micropolyspora sp. SANK 60983 (FERM BP-538, FERM P-6985) in a culture broth therefor at a temperature of from 24° to 30° C. at which said microorganism is viable to produce a sufficient amount of chloropolysporin in said culture broth and collecting said chloropolysporin from said culture broth.

3. A process as claimed in claim 2, wherein said temperature is about 28° C.

4. A pharmaceutical composition comprising a pharmaceutically effective amount of the antibiotic substance chloropolysporin as defined in claim 1 in admixture with a pharmaceutical carrier or diluent.

5. A method for the treatment or prophylaxis of bacterial infections by administering an antibiotically effective amount of the antibiotic substance chloropolysporin as defined in claim 1 to an animal.

6. A method of promoting the growth of a farm animal by the oral administration thereto of an antibiotically effective amount of the antibiotic substance chloropolysporin as defined in claim 1.

7. A veterinary composition comprising a veterinary effective amount of the antibiotic substance chloropolysporin as defined in claim 1 in admixture with a veterinary carrier or diluent.

* * * * *